United States Patent
Pettersen

(10) Patent No.: US 10,689,387 B2
(45) Date of Patent: Jun. 23, 2020

(54) CRYSTALLINE FORM OF (1R,2R)-2-[4-(3-METHYL-1H-PYRAZOL-5-YL)BENZOYL]-N-(4-OXO-4,5,6,7-TETRAHYDROPYRAZOLO[1,5-A]PYRAZIN-3-YL)CYCLOHEXANECARBOXAMIDE

(71) Applicant: AstraZeneca AB, Södertälje (SE)

(72) Inventor: Anna Matilda Angelica Pettersen, Mölndal (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 16/345,016

(22) PCT Filed: Oct. 27, 2017

(86) PCT No.: PCT/EP2017/077602
§ 371 (c)(1),
(2) Date: Apr. 25, 2019

(87) PCT Pub. No.: WO2018/078097
PCT Pub. Date: May 3, 2018

(65) Prior Publication Data
US 2019/0276460 A1 Sep. 12, 2019

Related U.S. Application Data

(60) Provisional application No. 62/414,109, filed on Oct. 28, 2016.

(51) Int. Cl.
*A61K 31/4985* (2006.01)
*C07D 487/04* (2006.01)
*A61P 9/00* (2006.01)
*C07D 231/50* (2006.01)
*C07D 231/40* (2006.01)
*C07D 413/12* (2006.01)
*C07D 498/04* (2006.01)
*C07D 231/44* (2006.01)
*A61K 31/4155* (2006.01)
*C07D 417/12* (2006.01)

(52) U.S. Cl.
CPC ........ *C07D 487/04* (2013.01); *A61K 31/4155* (2013.01); *A61P 9/00* (2018.01); *C07D 231/40* (2013.01); *C07D 231/44* (2013.01); *C07D 231/50* (2013.01); *C07D 413/12* (2013.01); *C07D 417/12* (2013.01); *C07D 498/04* (2013.01); *C07B 2200/13* (2013.01)

(58) Field of Classification Search
CPC .......................... A61K 31/4985; C07D 487/04
USPC ......................................... 514/250; 544/350
See application file for complete search history.

(56) References Cited

FOREIGN PATENT DOCUMENTS

WO 2016177703 A1 11/2016

OTHER PUBLICATIONS

Hoffman, Bettina et al., 5-Lipoxygenase inhibitors: a review of recent patents (2010-2012), Expert Opinion on Therapeutic Patents, (2013), 23:7, pp. 895-909.
Pergola, C. et al., 5-Lipoxygenase inhibitors: A review of recent developments and patents, Expert Opinion on Therapeutic Patents, (2010), 20:3, pp. 355-375.
Pettersen, et al., Recent Advances for Flap inhibitors, Bioorganic & Medicinal Chemistry Letters, (2015), vol. 25, pp. 2607-2612.
Written Opinion for PCT/EP2017/077602 dated Dec. 14, 2017.
International Search Report for PCT/EP2017/077602 dated Dec. 14, 2017.

*Primary Examiner* — Jeffrey H Murray

(57) ABSTRACT

A crystalline form of (1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide, pharmaceutical compositions containing it and its use in the prevention or treatment of cardiovascular diseases.

8 Claims, 2 Drawing Sheets ered-tk
CRYSTALLINE FORM OF (1R,2R)-2-[4-(3-METHYL-1H-PYRAZOL-5-YL)BENZOYL]-N-(4-OXO-4,5,6,7-TETRAHYDROPYRAZOLO[1,5-A]PYRAZIN-3-YL)CYCLOHEXANECARBOXAMIDE This application relates to a new physical form of (1R,2R)-2-[4-(3-methyl-1H-pyrazol-5-yl)benzoyl]-N-(4-oxo-4,5,6,7-tetrahydropyrazolo[1,5-a]pyrazin-3-yl)cyclohexanecarboxamide, to pharmaceutical compositions containing it and its use in therapy.

FLAP, 5-lipoxygenase activating protein, plays a critical role in the production of leukotrienes by the 5-lipoxygenase (5-LO) pathway. In particular, FLAP mediates the transfer of the substrate, arachidonic acid, released from membrane phospholipids to the active site of 5-LO. Leukotrienes are lipid mediators released by leukocytes, in particular neutrophils, eosinophils, mast cells and monocyte/macrophages. They belong to the wider class of lipid mediators known as eicosanoids, formed from arachidonic acid released from cell membranes. Two distinct classes of leukotriene exist, $LTB_4$ and CysLTs ($LTC_4$, $LTD_4$ and $LTE_4$). Functions of $LTB_4$ include chemo-attraction and activation of leukocytes, inhibition of neutrophil apoptosis, and activation of adhesion molecule expression. Such effects are mediated through binding to one of two distinct G protein-coupled receptors (BLT1 and BLT2) which differ in their affinity and specificity for $LTB_4$. Cysteinyl leukotrienes have vaso-active properties and can affect blood flow and vasopermeability, actions that are mediated by two CysLT receptors, CysLT1 and CysLT2.

To initiate leukotriene biosynthesis, 5-LO translocates to intracellular membranes such as the nuclear membrane where it interacts with FLAP. Arachidonic acid released from membrane phospholipids by cytoplasmic PLA2 ($cPLA_2$) is transferred via FLAP to 5-LO which then stereospecifically incorporates oxygen at the fifth carbon position, with the formation of 5(S)-HpETE. This is subsequently converted by 5-LO to $LTA_4$, the common precursor for leukotriene $B_4$ ($LTB_4$) and the cysteinyl leukotrienes ($LTC_4$, $LTD_4$ and $LTE_4$). The conversion of $LTA_4$ to $LTB_4$ is mediated by $LTA_4$ Hydrolase ($LTA_4H$), a zinc-dependent epoxide hydrolase. Formation of cysteinyl leukotrienes involves conjugation of $LTA_4$ to glutathione, mediated by $LTC_4$ synthase in cell membranes in association with FLAP, and the resulting $LTC_4$ may be further processed to $LTD_4$ and $LTE_4$ via peptidase activities.

Compounds that inhibit the function of either 5-LO or FLAP can result in the inhibition of leukotriene production. FLAP inhibitors bind directly to FLAP in cell membranes and prevent leukotriene biosynthesis by preventing the membrane translocation of 5-LO and/or the supply of arachidonic acid substrate to its active site. In this way, inhibition of FLAP prevents the production of both $LTB_4$ and CysLTs by inhibiting production of the common precursor $LTA_4$. Distinct from 5-LO inhibitors, FLAP inhibitors do not directly suppress oxidation of arachidonic acid by 5-LO and do not inhibit leukotriene production in lysed cell extracts.

Despite the availability of drugs that deal with risk factors such as high cholesterol levels and elevated blood pressure, further treatment options are needed to reduce atherosclerotic cardiovascular disease and its sequellae. The role of lipid deposition in the formation of atherosclerotic plaques is well-established. However, another key factor in atherogenesis is inflammation, including both the recruitment of inflammatory cells to atherosclerotic lesions and their activation within plaques. Pharmacological approaches that target inflammation could therefore provide a novel approach to treating patients with atherosclerosis. Inhibition of leukotriene production by means of administering a FLAP inhibitor is one such approach.

Another risk factor associated with cardiovascular disease is microvascular dysfunction. By attenuating leukocyte activation and interaction with the microvasculature in addition to reducing the production of vasoactive cysteinyl leukotrienes, pharmacological inhibition of FLAP could improve microvascular function in cardiovascular disease patients.

A link between FLAP, 5-LO pathway activity, leukotriene production and cardiovascular disease is supported by the following lines of evidence: 1) expression and activity of the 5-LO pathway increases in association with atherosclerotic plaque progression and symptoms of plaque instability that could cause plaque rupture and thrombosis leading to myocardial infarction (MI) (Spanbroek et al (2003) *PNAS* 100, 1238; Cipollone et al (2005) ATVB 25, 1665); 2) leukotriene levels in blood and urine are elevated in the period following a recent acute coronary syndrome (ACS) event (Sanchez-Gala et al (2009) *Cardiovascular Research* 81, 216; Carry et al (1992) *Circulation* 85, 230); 3) genetic haplotypes in the FLAP (ALOX5AP) gene are significantly associated with the risk of myocardial infarction (Helgadottir et al (2004) *Nature Genetics* 36, 233).

Many companies over the course of the last few decades have pursued FLAP as a target, and patent filings associated with these efforts are summarized in various publications. See e.g., Pergola & Werz, *Expert Opin. Ther. Patents* (2010) 20(3); and Hofmann & Steinhilber *Expert Opin. Ther. Patents*, (2013) 23(7) and Whatling, *Bioorg. Med. Chem. Lett.* (2015) 25(2607).

This application relates to a crystalline form of (1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide. This compound is structurally distinct from the compounds in the disclosures described above.

In the formulation of drug substances, it is important for the drug substance (active compound) to be in a form in which it can be conveniently handled and processed. This is of importance, not only from the point of view of obtaining a commercially-viable manufacturing process for the drug substance itself, but also from the point of view of subsequent manufacture of pharmaceutical formulations comprising the active compound and suitable excipients. In this connection, the chemical stability and the physical stability of the active compound are important factors. The active compound, and formulations containing it, should be capable of being effectively stored over appreciable periods of time, without exhibiting any significant change in the physico-chemical characteristics (e.g. chemical composition, density, hygroscopicity and solubility) of the active compound.

The structure of (1R,2R)-2-[4-(3-methyl-1H-pyrazol-5-yl)benzoyl]-N-(4-oxo-4,5,6,7-tetrahydropyrazolo[1,5-a]pyrazin-3-yl)cyclohexanecarboxamide (hereafter "Compound (I)") is shown below:

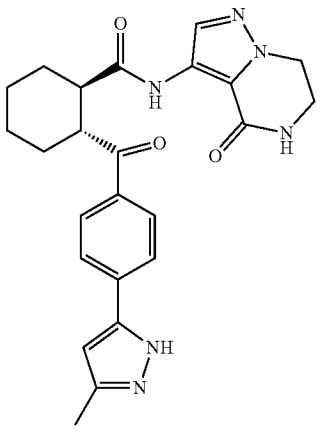

Compound (I)

We have found that Compound (I) may exist as a crystalline form. One crystalline form of Compound (I) "Form A" provides an X-ray powder diffraction pattern substantially as shown in FIG. 1. As the person of skill in the art will appreciate Compound (I) can exist in two tautomeric forms in which the pyrazole N—H is attached to either of the adjacent pyrazole ring nitrogens. Reference to Compound (I) explicitly encompasses both tautomeric forms.

One aspect provides a crystalline form of Compound (I).

Another aspect provides a physical form of Compound (I) form A.

Another aspect provides a physical form of Compound (I) form A, which exhibits the characteristic X-ray powder diffraction peaks (expressed in degrees 2θ) as shown in the appropriate Table 1 below, using CuKα radiation.

Another aspect provides crystalline form of Compound (I) for use in the manufacture of a medicament.

Another aspect provides crystalline form of Compound (I) for use in the manufacture of a medicament for use in the prevention or treatment of cardiovascular disease.

Unless stated otherwise, all of the X-ray powder diffraction data described herein was obtained using CuKα radiation as described in the Examples.

In one embodiment, the compound has crystalline properties and in one aspect is at least 50% crystalline, in another aspect is at least 60% crystalline, in another aspect is at least 70% crystalline, in another aspect is at least 80% crystalline and in another aspect is 90% crystalline. Crystallinity may be estimated by conventional X-ray diffractometry techniques.

In another embodiment, Compound (I) is from 60%, 70%, 80% or 90% to 95%, 96%, 97%, 98%, 99% or 100% crystalline.

The most prominent peaks of Compound (I) Form A are at 2θ about =9.7, 15.8, 17.3, 19.5 and/or 24.8°.

According to a further aspect, there is provided Compound (I) Form A, characterised in that said Form A has an X-ray powder diffraction pattern with at least one specific peak at 2θ about =9.7, 15.8, 17.3, 19.5 and/or 24.8°.

According to a further aspect, there is provided Compound (I) Form A, characterised in that said Form A has an X-ray powder diffraction pattern with at least 2 specific peaks at 2θ about =9.7, 15.8, 17.3, 19.5 and/or 24.8°.

According to a further aspect, there is provided Compound (I) Form A, characterised in that said Form A has an X-ray powder diffraction pattern with at least 3 specific peaks at 2θ about =9.7, 15.8, 17.3, 19.5 and/or 24.8°.

According to a further aspect, there is provided Compound (I) Form A, characterised in that said Form A has an X-ray powder diffraction pattern with at least one specific peak at 2θ about =9.7, 10.6, 15.8, 16.7, 17.3, 18.7, 19.5, 21.3, 23.3 and/or 24.8°.

According to a further aspect, there is provided Compound (I) Form A, characterised in that said Form A has an X-ray powder diffraction pattern with at least 2 specific peaks at 2θ about =9.7, 10.6, 15.8, 16.7, 17.3, 18.7, 19.5, 21.3, 23.3 and/or 24.8°.

According to a further aspect, there is provided Compound (I) Form A, characterised in that said Form A has an X-ray powder diffraction pattern with at least 3 specific peaks at 2θ about =9.7, 10.6, 15.8, 16.7, 17.3, 18.7, 19.5, 21.3, 23.3 and/or 24.8°.

According to a further aspect, there is provided Compound (I) Form A, characterised in that said Form A has an X-ray powder diffraction pattern with specific peaks at 2θ about =9.7, 15.8, 17.3, 19.5 and 24.8°

According to a further aspect, there is provided Compound (I) Form A, characterised in that said Form A has an X-ray powder diffraction pattern with specific peaks at 2θ about =9.7, 10.6, 15.8, 16.7, 17.3, 18.7, 19.5, 21.3, 23.3 and 24.8°.

According to a further aspect, there is provided Compound (I) Form A, characterised in that said Form A has an X-ray powder diffraction pattern substantially as shown in FIG. 1.

When heated in a Differential Scanning calorimeter (DSC) (conditions as described in the Examples section) the Compound (I) Form A exhibits a melting with an onset temperature at about 239.4° C., and a peak temperature at about 242.6° C. as illustrated in FIG. 2.

A person skilled in the art understands that the value or range of values observed in a particular compound's DSC Thermogram will show variation between batches of different purities. Therefore, whilst for one compound the range may be small, for others the range may be quite large. Generally, a measurement error of a diffraction angle in DSC thermal events is approximately plus or minus 5° C., and such degree of a measurement error should be taken into account when considering the DSC data included herein.

Therefore, in one embodiment there is provided a crystalline form, Compound (I) Form A, which has a DSC endotherm with an onset of melting at about 239.4° C. and a peak at about 242.6° C.

Therefore, in one embodiment there is provided a crystalline form, Compound (I) Form A, which has a DSC endotherm with an onset of melting at 239.4° C. plus or minus 5° C. and a peak at 242.6° C. plus or minus 5° C.

In one embodiment there is provided a crystalline form, Compound (I) Form A, which has a DSC endotherm with an onset of melting at 239.4° C. and a peak at 242.6° C. In one embodiment there is provided a crystalline form, Compound (I) Form A, which has a DSC thermogram substantially as shown in FIG. 2.

Crystallisation of the Form A in the process described herein may be aided by seeding with crystals of the Form A. The seed crystals may be obtained using one of the methods described in the Examples. The use of seeding is particularly advantageous in larger-scale manufacture.

Where herein the compound described as having "X-ray powder diffraction pattern with at least one specific peak at 2θ about = . . . " the XRPD of the compound may contain one or more of the 2θ values listed. For example one or more of the 2θ values, 2 or more of the 2θ values or 3 or more of the 2θ values listed.

In the preceding paragraphs defining the X-ray powder diffraction peaks for the crystalline form of Compound (I), the term "about =" is used in the expression " . . . at 2θ about = . . . " to indicate that the precise position of peaks (i.e. the recited 2-theta angle values) should not be construed as being absolute values because, as will be appreciated by those skilled in the art, the precise position of the peaks may vary slightly between one measurement apparatus and another, from one sample to another, or as a result of slight variations in measurement conditions utilised. It is also stated in the preceding paragraphs that the crystalline form of Compound (I) provide X-ray powder diffraction patterns 'substantially' the same as the X-ray powder diffraction patterns shown in FIG. 1 has substantially the most prominent peaks (2-theta angle values) shown in Table 1. It is to be understood that the use of the term 'substantially' in this context is also intended to indicate that the 2-theta angle values of the X-ray powder diffraction patterns may vary slightly from one apparatus to another, from one sample to another, or as a result of slight variations in measurement conditions utilised, so the peak positions shown in the Figure or quoted in the Table are again not to be construed as absolute values.

The person skilled in the art of X-ray powder diffraction will realize that the relative intensity of peaks can be affected by, for example, grains above approximately 30 micrometer in size and non-unitary aspect ratios which may affect analysis of samples. Furthermore, it should be understood that intensities may fluctuate depending on experimental conditions and sample preparation such as preferred orientation of the particles in the sample. The use of automatic or fixed divergence slits will also influence the relative intensity calculations. A person skilled in the art can handle such effects when comparing diffraction patterns.

The person skilled in the art of X-ray powder diffraction will also realize that due to difference in sample heights and errors in the calibration of the detector position, a small shift in the 2θ positions could occur. Generally, a difference of ±0.1° from the given value are to be considered correct.

Compound (I) Form A described herein may also be characterised and/or distinguished from other physical forms using other suitable analytical techniques, for example NIR spectroscopy or solid-state nuclear magnetic resonance spectroscopy.

The chemical structure of Compound (I) Form A described herein can be confirmed by routine methods for example proton nuclear magnetic resonance (NMR) analysis.

Compound (I) Form A may be prepared as described in the Example hereinafter.

Medical and Pharmaceutical Use

A crystalline form of compound (I) may be useful in the prevention or treatment of cardiovascular disease in a mammal, particularly a human. Cardiovascular disease includes, but is not limited to, conditions associated with cardiac dysfunction and/or microvascular dysfunction and/or macrovascular pathology, such as atherosclerosis, arteriosclerosis, coronary artery disease including stable and high risk coronary artery disease (defined as recent acute coronary syndrome (ACS) or by biomarkers of microvascular and cardiac dysfunction), myocardial infarction, restenosis following revascularization procedures, heart failure, abdominal aortic aneurysm (AAA), peripheral artery disease (PAD) including erectile dysfunction due to vascular disease, stroke, transient ischemic attack (TIA) and reversible ischemic neurologic disease (RIND), multi-infarct dementia and renal arterial disease. In particular, a crystalline form of a compound (I) may be useful in the prevention or treatment of high risk coronary artery disease.

A crystalline form of compound (I) may be useful in the prevention or treatment of patients with remaining risk for a cardiovascular event despite standard of care (SoC) treatment, such as, but not limited to, lipid lowering statins, anti-platelets, ACS inhibitors and beta blockers.

A crystalline form of compound (I) may be useful in the prevention or treatment of chronic kidney disease.

A crystalline form of compound (I) may be useful in the prevention or treatment of type II diabetes mellitus and complications of type II diabetes mellitus in a mammal, particularly a human. This includes and is not restricted to, diabetic micro and macrovascular pathology, neuropathy and nephropathy.

A crystalline form of compound (I) may be useful in the prevention or treatment of respiratory inflammatory disease and complications associated with respiratory inflammatory disease in a mammal, particularly a human. Respiratory inflammatory disease includes, but is not limited to asthma, chronic obstructive pulmonary disease, emphysema and rhinitis.

A crystalline form of compound (I) may be useful in the prevention or treatment of renal inflammatory and vascular diseases and complications associated with renal disease in a mammal, particularly a human. Renal inflammatory and vascular disease includes, but is not limited to chronic kidney disease, drug and toxin induced nephrotoxicity, glomerulonephritis, nephrotic syndrome, IgA nephritis, reflux nephropathy, focal segmental glomerulosclerosis, Henoch-Schönleins purpura, and diabetic nephropathy.

A crystalline form of compound (I) may be useful in the prevention or treatment of non-alcoholic fatty liver disease (NAFLD) and non-alcoholic steatohepatitis (NASH).

Treatment with a crystalline form of compound (I) may lower the cardiovascular and/or cerebrovascular and/or renal and/or peripheral arterial disease morbidity and mortality associated with cardiac dysfunction and/or microvascular dysfunction and/or macrovascular pathology due to their anti-inflammatory properties and influence on vasoactive mechanisms.

A crystalline form of compound (I) may serve to prevent or reduce the risk of developing cardiac dysfunction and/or microvascular dysfunction and/or macrovascular pathology, as well as for halting or slowing the progression and/or promoting the regression of atherosclerotic cardiovascular disease once it has become clinically evident, comprising the administration of a prophylactically or therapeutically effective amount, as appropriate, of a compound (I) to a mammal, including a human, who is at risk of developing atherosclerosis or who already has atherosclerotic cardiovascular disease.

A crystalline form of compound (I) may be useful in preventing or reducing the incidence or severity of acute events related to atherosclerotic plaque rupture or erosion, including, but not limited to, myocardial infarction, unstable angina and stroke.

A crystalline form of compound (I) may be useful in preventing or reducing the incidence or severity of acute events by improving microvascular function, macrovascular pathology and/or cardiac function.

A crystalline form of compound (I) may be useful in preventing or reducing the progression of abdominal aortic aneurysms (AAA) and incidence of rupture.

For the avoidance of doubt, as used herein, the term "treatment" includes therapeutic and/or prophylactic treatment. "Treatment" also includes administration of Compound (I) in order to alleviate symptoms of cardiovascular disease (including coronary artery disease and high risk coronary artery disease) and/or to lessen the severity of, or progression of, the same.

The compound disclosed herein may be thus indicated both in the therapeutic and/or prophylactic treatment of these conditions.

A crystalline form of compound (I) Form A may be useful for the manufacture of a medicament. In one embodiment, a crystalline form of compound (I) may be useful for the manufacture of a medicament for use in the prevention or treatment of cardiovascular disease, such as coronary artery disease or high risk coronary artery disease. In such manufacture, the storage stability of compound (I) Form A renders this form useful as an intermediate. For example, the compound (I) form A can be combined with excipients such as bulking agents, lubricating agents, binders and the like in the preparation of a tablet, capsule or other suitable dosage form without, or without substantial amounts of, degradation in storage or in processing. The compound (I) form A can also function as a stable intermediate for storage prior to final processing to deliver a medicament, for example prior to formation of a solution, a suspension or another physical form of compound (I).

Combination Therapy

A crystalline form of compound (I) may also be administered in conjunction with other compounds used for the treatment of the above conditions.

In another embodiment, there is a combination therapy wherein a compound of a crystalline form of compound (I), and a second active ingredient are administered concurrently, sequentially or in admixture, for the treatment of one or more of the conditions listed above. Such a combination may be used in combination with one or more further active ingredients.

A crystalline form of compound (I) described herein may be of use in treating cardiovascular, metabolic and renal disease in combination with agents that are
  cardiac therapies,
  anti-hypertensives,
  diuretics,
  peripheral vasodilators,
  lipid modifying agents,
  anti-diabetic,
  anti-inflammatory
  anti-oxidative
  anti-coagulant
  anti-thrombotic
  anti-platelet Examples of the above include, but are not restricted to, digitalis glycosides, anti-arrhythmics, calcium channel antagonists, ACE inhibitors, angiotensin receptor blockers (e.g. candesartan), endothelin receptor blockers, β-blockers, thiazide diuretics, loop diuretics, cholesterol synthesis inhibitors such as statins (e.g. Rosuvastatin), cholesterol absorption inhibitors, PPAR modulators, FXR agonists, cholesterylester transfer protein (CETP) inhibitors, anti-diabetic drugs such as insulin and analogues, GLP-1 analogues, sulphonamides, dipeptidyl peptidase 4 inhibitors, thiazolidinediones, sodium glucose transport protein (SGLT) inhibitors including SGLT2 (e.g. dapagliflozin), SGLT1, SGLT1/2, and anti-inflammatory drugs such as NSAID's and CCR2 antagonists, anti-oxidants such as vitamin E and SOD mimetics, anti-coagulants such as heparins, thrombin inhibitors and inhibitors of factor Xa, anti-thrombotics such as as tPA, platelet aggregation inhibitors (e.g., P2Y12 antagonists or ticagrelor) and neprilysin inhibitors (e.g. Sacubitril).

When used in a combination therapy, it is contemplated that a crystalline form of compound (I), and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians, and others skilled in the art.

Administration

There is provided a method of treatment of a condition where inhibition of FLAP is required, which method comprises administration of a therapeutically effective amount of a crystalline form of compound (I) to a person suffering from, or susceptible to, such a condition.

A crystalline form of compound (I), will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient in a pharmaceutically acceptable dosage form. Depending upon the disorder and patient to be treated and the route of administration, the compositions may be administered at varying doses.

Dosage forms suitable for oral use form one aspect of the invention.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, granulating and disintegrating agents such as corn starch; binding agents such as starch; lubricating agents such as magnesium stearate. Tablet formulations may be uncoated or coated using conventional coating agents and procedures well known in the art.

For further information on formulation the reader is referred to Chapter 25.2 in Volume 5 of *Comprehensive Medicinal Chemistry* (Corwin Hansch; Chairman of Editorial Board), Pergamon Press 1990.

The amount of active ingredient that is combined with one or more excipients to produce a single dosage form will necessarily vary depending upon the host treated and the particular route of administration.

Suitable daily doses of a crystalline form of compound (I), in therapeutic treatment of humans are about 0.0001-100 mg/kg body weight, preferably 0.01-30 mg/kg body weight.

Oral formulations are preferred particularly tablets or capsules which may be formulated by methods known to those skilled in the art to provide doses of the active compound in the range of 0.1 mg to 1000 mg for example 1 mg, 3 mg, 5 mg, 10 mg, 25 mg, 50 mg, 100 mg, 250 mg and 500 mg.

For further information on Routes of Administration and Dosage Regimes the reader is referred to Chapter 25.3 in Volume 5 of *Comprehensive Medicinal Chemistry* (Corwin Hansch; Chairman of Editorial Board), Pergamon Press 1990.

According to a further aspect, there is thus provided a pharmaceutical composition including a crystalline form of compound (I) in admixture with pharmaceutically acceptable adjuvants, diluents and/or carriers.

Biological Tests

The following test procedures may be employed:

FLAP Binding Assay (Test A)

Compounds were tested in a competition binding assay using $^3$H-MK591 as tracer. (Preparation of MK-591 is described in Bioorg. Med. Chem. Lett. 1999, 9, 2391). A 100,000×g pellet from COS-7 cells stably transfected with a plasmid expressing human ALOX5AP was the source of FLAP. Membrane pellets were resuspended in buffer (100 mM Tris-HCl, 0.05% Tween-20, 140 mM NaCl, 2 mM EDTA, 0.5 mM DTT, 5% Glycerol, pH 7.5) to give a final protein concentration of 12 mg/mL (2 μg/well). To perform assays, 1.4 μL compounds were dispensed into 96-well plates in 3-fold dilution series in triplicate. 84 μL radioligand (25000 CPM, 2 nM final concentration in assay) was then added followed by 84 μL membrane suspension and incubation at ambient temperature for 60 min. Following filtration, filter plates were dried 12 h at RT (or 50° C. for 1 hour). 50 μL scintillant was then added, the filterplates were sealed and radioactivity was measured in a microbeta counter. Specific binding was defined as total binding minus non-specific binding. Total binding was defined as $^3$H-MK591 bound to membranes in the absence of competitor, non-specific binding was defined as $^3$H-MK591 in the presence of 0.1 mM MK-591. $IC_{50}$ values were determined by plotting % inhibition versus log compound concentration and using a one site dose response model. Compound (I) is 6.3 IC50 nM.

FLAP Whole Blood Assay (Test B)

Compounds were tested for the inhibition of $LTB_4$ production in fresh human whole blood obtained by venapuncture using heparin to prevent clotting. 1.5 μL compounds or DMSO carrier were dispensed into the wells of a 96-well deep-well plate in 3-fold dilution series. 500 μL heparinised whole blood was then added followed by incubation at 37° C. for 30 min (method A) or 4 h (method B). 100 μL blood was subsequently transferred in triplicate to pre-dispensed 0.5 μL 2 mM calcium ionophore (calcimycin; A23187) in a second 96-well plate. Following incubation at 37° C. for 20 min, the assays were stopped by adding 10 μL of stop solution (100 mM EGTA, pH 7.4) and the plate was transferred to ice. The plate was centrifuged at 3000 rpm at 4° C. for 10 min and 10 μL plasma was transferred to a fresh 96 well plate containing 90 μL pre-dispensed EIA assay buffer (0.1 M phosphate buffer+0.1% BSA). $LTB_4$ was then measured using reagents from a commercial EIA (Cayman Chemicals). $LTB_4$ production was defined as the $LTB_4$ level in the presence of a given concentration of test compound minus the $LTB_4$ level in the presence of 50 nM 5-[[4-[(2S,4R)-4-hydroxy-2-methyl-tetrahydropyran-4-yl]-2-thienyl]sulfanyl]-1-methyl-indolin-2-one. (Preparation of 5-[[4-[(2S,4R)-4-hydroxy-2-methyl-tetrahydropyran-4-yl]-2-thienyl]sulfanyl]-1-methyl-indolin-2-one was described in Org. Process Res. Dev., 2005, 9, 555-569 or EP623614 B1). Inhibition of $LTB_4$ production was defined as the $LTB_4$ level in the presence of a given concentration of test compound expressed as a % of the $LTB_4$ level in the presence of DMSO. $IC_{50}$ values were determined by plotting % inhibition versus log compound concentration and using a one site dose response model. Compound (I) is 40 IC50 using method B.

EXAMPLES

Figure 1:
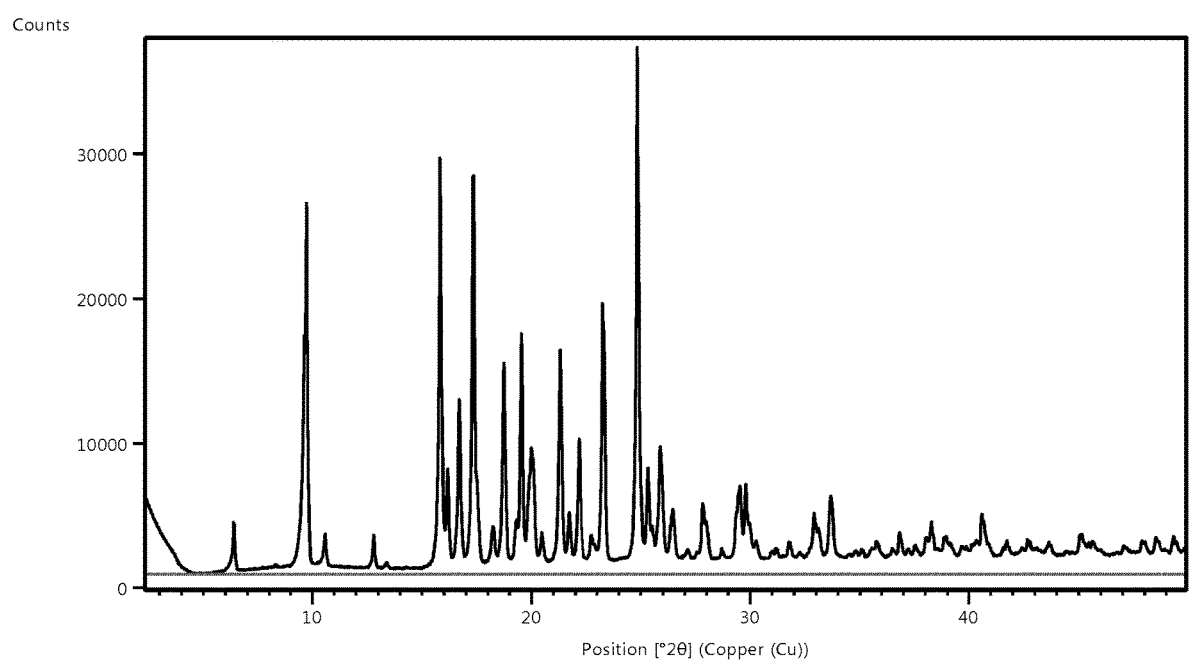
FIG. 1 shows an X-ray powder diffraction pattern of Example 1 (Form A).

The present invention will now be further explained by reference to the following illustrative examples in which, unless stated otherwise:

(i) Temperatures are given in degrees Celsius (° C.); operations were carried out at room or ambient temperature, that is, at a temperature in the range of 18-25° C.

(ii) In general, the course of reactions was followed by HPLC and reaction times are given for illustration only.

(iii) Yields are given for illustration only and are not necessarily those which can be obtained by diligent process development; preparations were repeated if more material was required.

(iv) Chemical symbols have their usual meanings; SI units and symbols are used.

(v) Solvent ratios are given in volume: volume (v/v) terms.

(vi) Unless stated otherwise, starting materials were commercially available.

X-Ray Powder Diffraction Analysis

A sample was mounted on single silicon crystal (SSC) wafer mount and powder X-ray diffraction was recorded with a Theta-Theta PANalytical X'Pert PRO (wavelength of X-rays 1.5418 Å nickel-filtered Cu radiation, Voltage 45 kV, filament emission 40 mA). Automatic variable divergence and anitscatter slits were used and the samples were rotated during measurement. Samples were scanned from 2-50° 2Theta using a 0.013° step width and a 233 seconds step measurement time using a PIXCEL detector (active length 3.35° 2Theta).

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins. R & Snyder. R. L. 'Introduction to X-Ray Powder Diffractometry' John Wiley & Sons. 1996).

Generally, a measurement error of a diffraction angle in an X-ray powder diffractogram may be approximately plus or minus 0.1° 2-theta, and such a degree of a measurement error should be taken into account when considering the X-ray powder diffraction data. Furthermore, it should be understood that intensities might fluctuate depending on experimental conditions and sample preparation (e.g. preferred orientation).). The following definitions have been used for the relative intensity (%): 81-100%, vs (very strong); 41-80%, str (strong); 21-40%, med (medium); 10-20%, w (weak); 1-9%, vw (very weak).

TABLE 1

Peaks of Compound (I) Form A

| Position °2theta | Intensity |
|---|---|
| 6.4 | vw |
| 9.6 | m |
| 9.7 | s |
| 10.6 | vw |
| 12.8 | vw |
| 15.8 | vs |
| 16.2 | w |
| 16.7 | m |
| 17.3 | s |
| 18.2 | vw |
| 18.7 | m |
| 19.3 | vw |
| 19.5 | s |
| 20.0 | m |
| 20.5 | vw |
| 21.3 | s |
| 21.7 | w |
| 22.2 | m |
| 23.3 | s |
| 24.8 | vs |
| 25.3 | m |
| 25.9 | m |
| 26.5 | w |
| 27.8 | w |

General Methods

The crystalline forms of the present application will now be further explained by reference to the following non limiting example.

In the examples, high resolution mass spectra were recorded on a Micromass LCT mass spectrometer equipped with an electrospray interface (LC-HRMS). $^1$H NMR measurements were performed on Varian UNITY plus 400, 500 and 600 spectrometers or Varian INOVA 400, 500 and 600 spectrometers or Bruker Avance 400, 500 and 600 spectrometers, operating at $^1$H frequencies of 400, 500 and 600 MHz, respectively. The experiments were typically recorded at 25° C. Chemical shifts are given in ppm with the solvent as internal standard. Flash chromatography was performed using straight phase flash chromatography on a SP1™ Purification system from Biotage™ using normal phase silica FLASH+™ (40M, 25M or 12 M) or SNAP™ KP-Sil Cartridges (340, 100, 50 or 10) unless otherwise stated. In general, all solvents used were commercially available and of analytical grade. Anhydrous solvents were routinely used for reactions. Phase Separators used in the examples are ISOLUTE® Phase Separator columns. The Intermediates and Examples named below were named using ACD/Name 12.01 from Advanced Chemistry Development, Inc. (ACD/Labs).

Experimental. DSC: Thermal events were analysed by modulated differential scanning calorimetry on a TA DSC Q2000 instrument. 9.7 mg of material contained in a standard aluminium closed cup with a pinhole was measured over the temperature range 0° C. to 260° C. at a constant heating rate of 5° C. per minute, with a overlayed modulation of 0.53° C. at a modulation interval of 40 seconds. A purge gas using nitrogen was used (flow rate 50 mL per minute). The melting point onset temperatures presented are not to be taken as absolute values. It is known that the melting point onset temperature may be affected by several parameters such as impurity content and particle size.

Abbreviations

The following abbreviations have been used:
AcOH acetic acid
Aq: aqueous
MeCN: acetonitrile
MeOH: methanol
DCM: dichloromethane
DMF: dimethylformamide
Et$_2$O: diethyl ether
EtOAc: ethyl acetate
MgSO$_4$: magnesium sulphate
NaHCO$_3$: sodium hydrogen carbonate
NH$_4$Cl: ammonium chloride
T3P: 2,4,6-tripropyl-1,3,5,2,4,6-trioxatriphosphinane 2,4,6-trioxide
TFA: trifluoroacetic acid Example 1

(1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide (Crystalline Form A)

(1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide methanol solvate, prepared as Intermediate 8 below, (6.070 kg, 13.19 mol) in acetone (66 L) and water (7.3 L) was heated to 55° C. then cooled to 30° C. and the solution filtered. This was then distilled at atmospheric pressure to about 24 L. 2-Methyltetrahydrofuran (36.5 L) was charged and distilled at atmospheric pressure to about 24 L. Further 2-methyltetrahydrofuran (36.5 L) was charged and distilled at atmospheric pressure to about 24 L. Further 2-methyltetrahydrofuran (36.5 L) was charged and distilled at atmospheric pressure to about 24 L. The suspension was cooled to 20° C. and resulting solid filtered and washed with 2-methyltetrahydrofuran (6.1 L). The solid was dried under vacuum at 60° C. to give the title compound (crystalline Form A) (5.679 kg, 12.40 mol, 94% yield).
$^1$H NMR (400 MHz, DMSO-d$_6$) δ 1.10-1.55 (m, 4H), 1.74-1.82 (m, 2H), 1.95-2.08 (m, 2H), 2.28 (s, 3H), 2.99 (t, 1H), 3.70 (s, 2H), 3.82 (t, 1H), 4.21 (t, 2H), 6.58 (s, 1H), 7.82 (s, 1H), 7.90 (d, 2H), 8.01 (d, 2H), 8.33 (s, 1H), 9.15 (s, 1H), 12.76 (s, 1H)

Intermediate 1: 3-Methyl-1-(tetrahydro-2H-pyran-2-yl)-5-(4,4,5,5-tetramethyl-1,3,2-dioxaborolan-2-yl)-1H-pyrazole

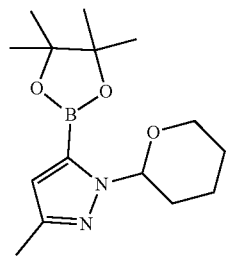 [SMILES: Cc1cc(B2OC(C)(C)C(C)(C)O2)n(C2CCCCO2)n1]

Step 1—3-Methyl-1-(tetrahydro-2H-pyran-2-yl)-1H-pyrazole

3-Methyl-1H-pyrazole (2 mL, 24.8 mmol) was dissolved in 3,4-dihydro-2H-pyran (6.8 mL, 74.5 mmol). Trifluoroacetic acid (0.134 mL, 1.74 mmol) was added and the clear solution was warmed to 75° C. for 18 h. The reaction mixture was diluted with Et$_2$O and the organic phase was washed with NaHCO$_3$(sat, aq), water and brine, filtered using a phase separator and concentrated in vacuo. The residue was purified by flash chromatography (10%→20% of EtOAc in heptane) to give the subtitle compound. (2.4 g, 58%, 70% correct isomer)

$^1$H NMR (500 MHz, CDCl$_3$) δ 7.44 (d, 1H), 7.40 (s, 0.3H), 6.04 (d, 1H), 6.00 (s, 0.3H), 5.21-5.28 (m), 3.94-4.09 (m), 3.57-3.68 (m), 2.47 (s, OH), 2.31 (s, 1H), 2.26 (s, 3H), 1.9-2.16 (m), 1.59-1.75 (m).

Step 2—3-Methyl-1-(tetrahydro-2H-pyran-2-yl)-5-(4,4,5,5-tetramethyl-1,3,2-dioxaborolan-2-yl)-1H-pyrazole n-Butyllithium (6.1 mL, 15.2 mmol, 2.5M in THF) was added during 10 min to a solution of 3-methyl-1-(tetrahydro-2H-pyran-2-yl)-1H-pyrazole (2.4 g, 14.4 mmol) in THF (20 mL) at −78° C. During a period of 15 min tripropan-2-yl borate (3.7 mL, 15.9 mmol) was added dropwise at −78° C. and the reaction mixture was stirred for 15 min, where after it was allowed to reach ambient temperature. 2,3-Dimethylbutane-2,3-diol (1.88 g, 15.9 mmol) was added followed by AcOH (1.65 mL, 28.9 mmol) and the reaction mixture was stirred at rt over night. The reaction mixture was diluted with heptane and the organic phase was washed with NH$_4$Cl (aq), NaHCO$_3$ (aq) and brine, filtered using a phase separator and concentrated. The residue was diluted with heptane and concentrated to give the title compound (3.86, 91%). MS m/z 293.2 [M+H]$^+$

Intermediate 2: (1R,2R)-2-{4-[3-Methyl-1-(tetrahydro-2H-pyran-2-yl)-1H-pyrazol-5-yl]benzoyl}cyclohexanecarboxylic Acid

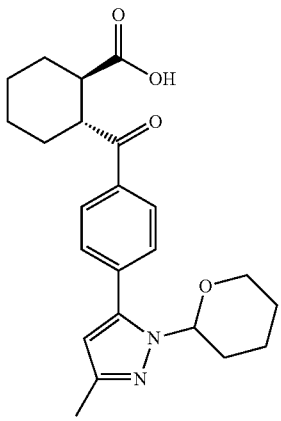 [SMILES: Cc1cc(-c2ccc(C(=O)[C@@H]3CCCC[C@H]3C(=O)O)cc2)n(C2CCCCO2)n1]

K$_2$CO$_3$ (4.02 g, 29.05 mmol) and Pd(dtbpf)Cl$_2$ (0.28 g, 0.36 mmol) were added to a solution of (1R,2R)-2-(4-bromobenzoyl)cyclohexanecarboxylic acid (2.26 g, 7.26 mmol) and 3-methyl-1-(tetrahydro-2H-pyran-2-yl)-5-(4,4,5,5-tetramethyl-1,3,2-dioxaborolan-2-yl)-1H-pyrazole (Intermediate 1, 3.18 g, 10.89 mmol) dissolved in 1,4-dioxane (40 mL) and water (20 mL). The mixture was evacuated and purged with nitrogen three times and then heated at 80° C. for 1 h. The mixture was cooled to rt and diluted with EtOAc. NaHCO$_3$ (sat, aq) was added and the mixture was acidified with KHSO$_4$ (1 M, aq). The phases were separated and the aqueous phase was extracted twice with EtOAc. The combined organic phase was dried using a phase separator and the solvent was removed under vacuum. The crude residue was purified by preparative HPLC on a Kromasil C8 column (10 μm 250×50 ID mm) using a gradient of 30%-90% MeCN in H$_2$O/MeCN/AcOH (95/5/0.2) buffer system as mobile phase. The selected fractions were combined and concentrated under vacuum and the aqueous residue was extracted twice with DCM. The combined organic phase was dried using a phase separator and the solvent was removed under vacuum to give the title compound (2.79 g, 97%) as a light brown solid.

$^1$H NMR (500 MHz, CDCl$_3$) δ 1.21-1.64 (m, 6H), 1.71-1.94 (m, 4H), 2.02-2.12 (m, 2H), 2.23-2.31 (m, 1H), 2.34 (s, 3H), 2.52-2.64 (m, 1H), 2.93-3.02 (m, 1H), 3.53-3.66 (m, 2H), 4.11-4.19 (m, 1H), 5.13 (dd, 1H), 6.18 (s, 1H), 7.56-7.63 (m, 2H), 8.01-8.07 (m, 2H) MS m/z 395.3 [M−H]$^−$

Intermediate 3: Methyl 4-[(tert-butoxycarbonyl)amino]-1H-pyrazole-5-carboxylate

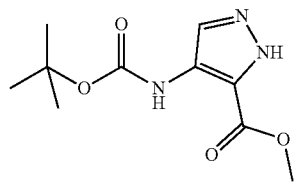 [SMILES: COC(=O)c1[nH]ncc1NC(=O)OC(C)(C)C]

Di-tert-Butyl dicarbonate (159 mL, 0.68 mol) was added to methyl 4-amino-1H-pyrazole-3-carboxylate (87.6 g, 0.62 mol) and pyridine (100 mL, 1.24 mol) in MeOH (1 L) at 10° C. over a period of 15 min. The reaction mixture was stirred at rt for 5 h. The solvent was removed under vacuum. The crude product was purified by crystallization from MeOH (700 mL) to give the title compound (80 g, 53%) as a purple solid.

MS m/z 228 [M+H]$^+$ $^1$H NMR (400 MHz, DMSO-d$_6$) δ 1.47 (s, 9H), 3.83 (s, 3H), 7.70-8.20 (m, 2H), 13.45 (s, 1H)

Intermediate 4: Methyl 1-(2-bromoethyl)-4-[(tert-butoxycarbonyl)amino]-1H-pyrazole-5-carboxylate

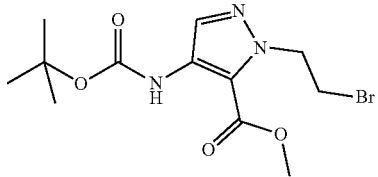 [SMILES: COC(=O)c1c(NC(=O)OC(C)(C)C)cnn1CCBr]

1,2-dibromoethane (1.97 mL, 22.8 mmol) was added to a solution of methyl 4-[(tert-butoxycarbonyl)amino]-1H-pyrazole-5-carboxylate (Intermediate 3, 5.0 g, 20.7 mmol) and K$_2$CO$_3$ (4.3 g, 31.1 mmol) in DMF (50 mL) at 0° C. over a period of 10 min and the reaction mixture was stirred at rt for 5 h. Water was added to the reaction mixture and the aqueous phase was extracted with EtOAc. The organic layer was dried over MgSO$_4$, filtered and evaporated and the crude product was purified by flash chromatography (5%→20% 2-methylpentane in EtOAc). Pure fractions were evaporated to dryness to give the title compound (2.5 g, 35%) as a colorless oil.

$^1$H NMR (300 MHz, DMSO-d$_6$) δ 1.47 (s, 9H), 3.80 (t, 2H), 3.87 (s, 3H), 4.79 (t, 2H), 7.86 (s, 1H), 8.24 (s, 1H)

MS m/z 348 [M+H]$^+$

Intermediate 5: tert-Butyl (4-oxo-4,5,6,7-tetrahydropyrazolo[1,5-a]pyrazin-3-yl)carbamate

Ammonia hydrate (10 g, 287.2 mmol) was added to a solution of methyl 1-(2-bromoethyl)-4-[(tert-butoxycarbonyl)amino]-1H-pyrazole-5-carboxylate (Intermediate 4, 10.0 g, 28.7 mmol) in MeCN (100 mL) and the reaction vessel was sealed and heated at 90° C. for 20 h. The solvent was removed under vacuum and the crude product was purified by flash chromatography, elution gradient (1%→10% DCM in MeOH). Pure fractions were evaporated to dryness to give the title compound (6.0 g, 83%) as a white solid. $^1$H NMR (400 MHz, DMSO-d$_6$) δ 1.47 (s, 9H), 3.60 (t, 2H), 4.22 (t, 2H), 7.76 (s, 1H), 7.95 (s, 1H), 8.30 (s, 1H)

MS m/z 253 [M+H]$^+$

Intermediate 6: 3-Amino-6,7-dihydropyrazolo[1,5-a]pyrazin-4(5H)-one hydrochloride

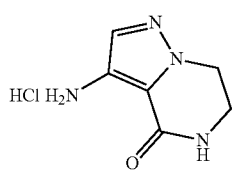

HCl (g) was added to a solution of tert-butyl (4-oxo-4,5,6,7-tetrahydropyrazolo[1,5-a]pyrazin-3-yl)carbamate (Intermediate 5, 9 g, 35.68 mmol) in MeOH (50 mL) and the reaction mixture was stirred at rt for 2 h. The precipitate was collected by filtration, washed with EtOAc and dried under vacuum to give the title compound (6.00 g, 89%) as a white solid.

MS m/z 153 [M+H]$^+$

Intermediate 7: (1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide HCl To (1R,2R)-2-{4-[3-methyl-1-(tetrahydro-2H-pyran-2-yl)-1H-pyrazol-5-yl]benzoyl}cyclohexanecarboxylic acid (Intermediate 2, 1.2 kg, 2.8 mol)) and 3-amino-6,7-dihydropyrazolo[1,5-a]pyrazin-4(5H)-one hydrochloride (Intermediate 6, 0.6 kg, 3 mol)) in ethyl acetate (7.8 L) was charged pyridine (1.5 kg, 19 mol). The mixture was cooled to 0-5° C. and then T3P (50% in ethyl acetate, 4.6 kg, 7.6 mmol) over 30 minutes maintaining the temperature below 5° C. The mixture was heated to 20° C. for 22 h then cooled to 10° C. Additonal ethyl acetate (5.6 L) was charged then water (5.6 L) maintaining the temperature below 15° C. The aqueous layer was removed and the organic phase washed with citric acid (0.28 kg, 1.5 mol) in water (5.3 L), citric acid (0.28 kg, 1.5 mol) in water (5.3 L), sodium hydrogen carbonate (0.28 kg, 3.3 mol) in water (5.3 L) and finally sodium chloride (1.5 kg, 25 mol) in water (4.2 L). The organic phase was distilled under vacuum, removing 7.8 L of distillate. 2-Methyltetrahydrofuran (6.4 L) was charged and the mixture distilled under vacuum, removing 6.1 L of distillate. Further 2-methyltetrahydrofuran (5.0 L) was charged followed by a solution of 37% hydrochloric acid (0.42 L) in water (2.1 L). The resulting precipitate was collected by filtration and washed with ~3 L of the mother liquors, then 2-methyltetrahydrofuran (2.2 L), then further 2-methyltetrahydrofuran (2.2 L). The resulting solid was dried under vacuum at ~40° C. to yield (1R,2R)-2-[4-(3-methyl-1H-pyrazol-5-yl)benzoyl]-N-(4-oxo-4,5,6,7-tetrahydropyrazolo[1,5-a]pyrazin-3-yl)cyclohexanecarboxamide HCl (1.012 kg, 1.970 mol, 70% yield).

1H NMR (500 MHz, DMSO, 27° C.) 1.18 (1H, dd), 1.33-1.58 (3H, m), 1.71-1.84 (2H, m), 1.96 (1H, dd), 2.05 (1H, dd), 2.28-2.37 (3H, m), 2.98 (1H, ddd), 3.60 (2H, ddd), 3.69-3.78 (1H, m), 4.22 (2H, dd), 6.73 (1H, d), 7.84 (1H, s), 7.94-7.99 (2H, m), 8.02-8.07 (2H, m), 8.35 (1H, d), 9.16 (1H, s).

Assigned Hs: 25.

Figure 2:
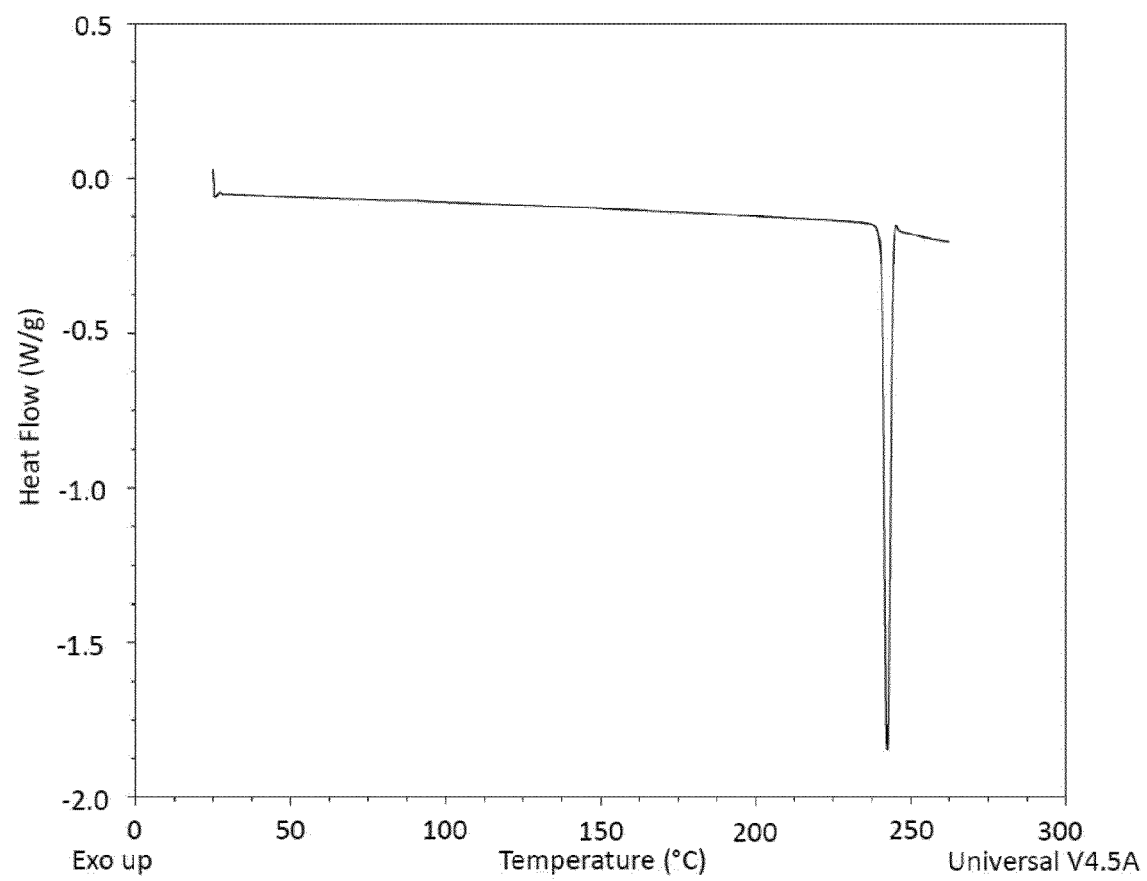
FIG. 2 shows DSC of Example 1 (Form A).

Intermediate 8: (1R,2R)-2-[4-(3-Methyl-1H-pyrazol-5-yl)benzoyl]-N-(4-oxo-4,5,6,7-tetrahydropyrazolo[1,5-a]pyrazin-3-yl)cyclohexanecarboxamide, Methanol Solvate To a suspension of (1R,2R)-2-[4-(3-methyl-1H-pyrazol-5-yl)benzoyl]-N-(4-oxo-4,5,6,7-tetrahydropyrazolo[1,5-a]pyrazin-3-yl)cyclohexanecarboxamide HCl (Intermediate 7, 2.25 kg, 4.43 mol) in methanol (11.3 L) and water (8.6 L) was added concentrated aqueous ammonia (0.54 L) over approximately 1 h. Further concentrated aqueous ammonia (2.2 L) was added over approximately 90 minutes. The mixture was stirred for 21 h at 20° C. and then filtered. The collected solid was washed with water (2.25 L×2). The damp solid was returned to the vessel and methanol (9 L) and water (9 L) charged. To the mixture was added concentrated aqueous ammonia (0.54 L) and the mixture stirred at 20° C. for 2.5 h and the resulting solid was collected by filtration. The collected solid was washed with water (2.25 L×2) then dried under vacuum at 60° C. to yield the title compound, Intermediate 8 (1.939 kg, 4.256 mol, 96% yield). DSC as shown in FIG. 2, DSC endotherm onset temperature 239.4° C. and peak at 242.6° C.

$^1$H NMR (400 MHz, DMSO-d$_6$) δ 1.10-1.55 (m, 4H), 1.74-1.82 (m, 2H), 1.95-2.08 (m, 2H), 2.28 (s, 3H), 2.99 (t, 1H), 3.70 (s, 2H), 3.82 (t, 1H), 4.21 (t, 2H), 6.58 (s, 1H), 7.82 (s, 1H), 7.90 (d, 2H), 8.01 (d, 2H), 8.33 (s, 1H), 9.15 (s, 1H), 12.76 (s, 1H)

The invention claimed is:

1. A crystalline form of (1R,2R)-2-[4-(3-methyl-1H-pyrazol-5-yl)benzoyl]-N-(4-oxo-4,5,6,7-tetrahydropyrazolo[1,5-a]pyrazin-3-yl)cyclohexanecarboxamide:

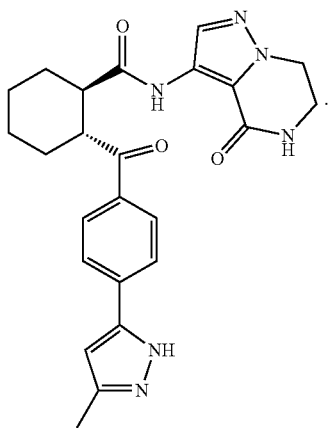 [SMILES: Cc1cc(-c2ccc(C(=O)[C@@H]3CCCC[C@H]3C(=O)Nc3cnn4c3C(=O)NCC4)cc2)[nH]n1]

2. A crystalline form according to claim 1, characterised in that it has that has an X-ray powder diffraction pattern with at least one specific peak at 2θ about =9.7, 10.6, 15.8, 16.7, 17.3, 18.7, 19.5, 21.3, 23.3 and/or 24.8° when measured using CuKα radiation.

3. A crystalline form according to claim 1, characterised in that it has an X-ray powder diffraction pattern with at least one specific peak at 2θ about =9.7, 15.8, 17.3, 19.5 and/or 24.8° when measured using CuKα radiation.

4. A crystalline form according to claim 1, characterised in that it has an X-ray powder diffraction pattern with specific peaks at 2θ about =9.7, 15.8, 17.3, 19.5 and 24.8° when measured using CuKα radiation.

5. A crystalline form according to claim 1, characterised in that it has an X-ray powder diffraction pattern with specific peaks at 2θ about =9.7, 10.6, 15.8, 16.7, 17.3, 18.7, 19.5, 21.3, 23.3 and 24.8° when measured using CuKα radiation.

6. A crystalline form according to claim 1, characterised in that it has an X-ray powder diffraction pattern substantially as shown in FIG. 1, when measured using CuKα radiation.

7. A pharmaceutical composition comprising a crystalline form as claimed in claim 1 and a pharmaceutically acceptable adjuvant, diluent or carrier.

8. A method of treating acute coronary syndrome comprising administering a crystalline form according to claim 1 to a patient in need thereof.

* * * * *